(12) United States Patent
Minoshima et al.

(10) Patent No.: US 6,399,059 B1
(45) Date of Patent: Jun. 4, 2002

(54) THERMALLY STABLE ENZYME COMPOSITION AND METHOD OF PREPARING THE SAME

(75) Inventors: Ryouichi Minoshima; Yoriko Endou, both of Yokohama (JP)

(73) Assignee: The Nisshin Oil Mills, Ltd., Tokyo (JP)

( * ) Notice: Subject to any disclaimer, the term of this patent is extended or adjusted under 35 U.S.C. 154(b) by 0 days.

(21) Appl. No.: 09/409,255

(22) Filed: Sep. 30, 1999

(30) Foreign Application Priority Data

Oct. 6, 1998 (JP) .......................................... 10-284211

(51) Int. Cl.$^7$ ........................ A61K 38/54; A61K 38/43; A61K 38/46; A61K 38/47; A61K 38/48
(52) U.S. Cl. .................... 424/94.3; 424/94.1; 424/94.2; 424/94.6; 424/94.61; 424/94.62; 424/94.63; 424/94.65; 424/94.66
(58) Field of Search ................................ 435/7, 14, 26, 435/177, 188, 810; 436/528, 535, 815; 424/401, 94.6, 94.1, 94.3, 94.2, 94.61, 94.66, 94.62, 94.65

(56) References Cited

U.S. PATENT DOCUMENTS

| | | | |
|---|---|---|---|
| 4,622,294 A | * | 11/1986 | Kung et al. .................... 435/7 |
| 4,783,400 A | * | 11/1988 | Canova-Davis et al. ....... 435/7 |

* cited by examiner

*Primary Examiner*—Jon P. Weber
*Assistant Examiner*—Patricia Patten
(74) *Attorney, Agent, or Firm*—Bacon & Thomas

(57) ABSTRACT

A thermally stable enzyme composition contains an enzyme, and a heat stabilizer including a phospholipid and an oil-soluble vitamin. The enzyme composition can be prepared in the form of a powder by drying an enzyme solution containing a phospholipid and an oil-soluble vitamin to obtain an enzyme powder.

27 Claims, No Drawings

THERMALLY STABLE ENZYME COMPOSITION AND METHOD OF PREPARING THE SAME

BACKGROUND OF THE INVENTION

The present invention relates to a thermally stable enzyme composition and a method of manufacturing the same, and more particularly, to an enzyme composition thermally stable in an aqueous solution and a method of manufacturing the same.

An enzyme can effect a catalytic reaction under milder conditions and exhibits a high substrate specificity, compared with a chemical reaction. Therefore, an enzyme is widely used in the fields of food industry, chemical industry, pharmaceutical industry, etc.

However, the enzyme is generally unstable. Particularly, the enzyme stability is low in a solution. It should be noted that a thermal denaturation begins to take place in many lipid-decomposing enzymes if these enzymes are exposed to temperatures exceeding about 35° C., making it difficult to utilize an enzyme in a reaction system using a substrate having a high melting point. Also, since an enzyme is thermally unstable, a freeze-drying method that is less likely to be affected thermally is utilized mainly for concentrating and preparing an enzyme powder. However, the freeze-drying method requires a tremendous facility investment for the mass production, resulting in a high running cost such as a utility cost.

For improving the thermal stability of the enzyme within an aqueous solution, it has been proposed to add a stabilizer to the enzyme. For example, it has been studied to add an amino acid such as albumin, casein, or sodium glutamate; a reducing agent such as protein, mercapto ethanol, or cysteine; a polyol such as glycerol, sucrose, or sorbitol; or a water-soluble high molecular weight substance such as dextran to an enzyme solution. Also proposed are a method of modifying an enzyme surface with, for example, an emulsifier or another amphoteric substance as disclosed in Japanese Patent Disclosure (Kokai) No. 6-113847, a method of modifying an enzyme surface with an oil-soluble substance having an isoprenoid structure as disclosed in Japanese Patent Disclosure No. 6-269285, and a method of stabilizing an enzyme by dissolving a phospholipid in an alcoholic solvent, followed by mixing the resultant solution with an enzyme and subsequently drying the mixture (Japanese Patent Disclosure No. 1-27719).

However, the lipid-decomposing enzyme obtained by the conventional methods described above is stable only under temperatures of about 37 to 60° C. and, thus, is relatively unstable under heat, making it relatively difficult to use the enzyme for an enzyme synthesis, etc. using a substrate having a high melting point. Also, in the method of preparing an enzyme powder by a spraying method, which is a typical drying method, the enzyme is concentrated under heat and, then, dried within a hot gaseous stream. Therefore, the enzyme activity is lowered.

BRIEF SUMMARY OF THE INVENTION

An object of the present invention is to provide a thermally stable enzyme composition exhibiting an improved heat resistance even within an aqueous solution and capable of stably performing an enzyme reaction under high temperatures.

Another object is to provide a method of preparing an enzyme composition that permits stably preparing an enzyme powder while preventing the enzyme activity from being lowered by the heat in the enzyme powder preparation even by a drying method under heat.

These objects can be achieved according to the present invention by adding a heat stabilizer comprising a combination of an oil-soluble vitamin and a phospholipid to an enzyme solution. The heat stability of the enzyme is significantly improved by adding a heat stabilizer including an oil-soluble vitamin and a phospholipid.

Thus, the present invention provides an enzyme composition comprising an enzyme and a heat stabilizer including a phospholipid and an oil-soluble vitamin.

The present invention also provides a method of preparing a thermally stable enzyme, comprising the step of drying an enzyme solution containing a phospholipid and an oil-soluble vitamin to obtain an enzyme powder. The drying should preferably be performed by a spray drying.

In a preferred embodiment of the present invention, the enzyme composition of the invention contains 0.01 to 200% by weight of a phospholipid and 0.01 to 100% by weight of an oil-soluble vitamin, based on the enzyme weight.

The enzyme used in the present invention should desirably be a lipid-decomposing enzyme. Also, it is desirable to use an oil-soluble vitamin selected from the group consisting of tocopherol, tocotrienol, retinol, calciferol, phylloquinone, and ubiquinone.

DETAILED DESCRIPTION OF THE INVENTION

The present invention provides a method of preparing an enzyme, in which a phospholipid and an oil-soluble vitamin are added to an enzyme solution to improve the thermal stability of the enzyme and which permits suppressing the deactivation of the enzyme by heat in a powder preparation by a drying method under heating to make it possible to prepare an enzyme powder.

The enzyme used in the present invention, which is not particularly limited, includes preferably a lipid-decomposing enzyme, protease, and sugar-decomposing enzyme. It is particularly desirable to use a lipid-decomposing enzyme. In addition to the enzyme formulations available on the market, the enzyme can be used in the present invention in the form of a microorganism culture solution, a plant extraction liquid and an animal cell extraction liquid. Further, a culture solution, a concentrated extraction liquid and a desalted concentrated solution can also be used as the enzyme in the present invention.

The lipid-decomposing enzyme used in the present invention includes lipases, phospholipases, and esterases. The lipases include, for example, lipoprotein lipase, monoacyl glycerollipase, diacyl glycerollipase, triacyl glycerollipase, and galactolipase. The phospholipases include, for example, lyso phospolipase, and phospholipases A1, A2, B, C and D. Further, the esterases include, for example, choline esterase, cholesterol esterase, pectin esterase, tropine esterase, acetylcholine esterase, acetyl esterase, carboxy esteradse, and aryl esterase.

The sugar-decomposing enzymes used in the present invention include, for example, amylase, glucosidase, cellulase, xylanase, dextranase, chitinase, lysozyme, galactosidase, mannosidase, glucuronidase, hyaluronidase and pectin lyase.

The protease used in the present invention includes endopectidases and exopeptidases. The endopectidases include, for example, acid proteinase, serine protease, cysteine protease, asparagic acid protease, thiol protease, and carboxy protease. On the other hand, the exopetidases include, for example, dipeptidylamino peptidase and dipeptidylcarboxy peptidase.

The microorganisms producing the enzymes used in the present invention, which are not particularly limited, can be selected from bacteria, yeasts, filamentous viruses, and actinomycetes, and include, for example, Psudomonas species, Alcaligenes species, Arthrobacter species, Staphylococcus species, Torulopsis species, Escherichia species, Micotorula species, Propionibacterum species, Chromobacterum species, Xanthomonas species, Lactobacillus species, Clostridium species, Candida species, Geotrichum species, Sacchromycopsis species, Nocardia species, Fuzarium species, Aspergillus species, Penicillium species, Mucor species, Rhisopus species, Phycomycese species, Puccinia species, Bacillus species and Streptmycese species.

A culture medium containing soybean powder, peptone, corn steep liquor, $K_2HPO_4$, $(NH_4)_2SO_4$, $MgSO_4.7H_2O$, etc. can be used for growing the microorganisms given above. It is. desirable for the culture medium to contain soybean powder in an amount of 0.1 to 20% by weight, preferably 1.0 to 10% by weight. Peptone should desirably be contained in an amount of 0.1 to 30% by weight, preferably 0.5 to 10% by weight. Corn steep liquor should desirably be contained in an amount of 0.1 to 30% by weight, preferably 0.5 to 10% by weight. $K_2HPO_4$ should desirably be contained in an amount of 0.01 to 20% by weight, preferably 0.1 to 5% by weight. $(NH_4)_2SO4$ should desirably be contained in an amount of 0.01 to 20% by weight, preferably 0.05 to 5% by weight. Further, $MgSO_4.7H_2O$ should desirably be contained in an amount of 0.01 to 20% by weight, preferably 0.05 to 5% by weight. Other culture media can also be used, as exemplified in the Examples described herein later. It is desirable to culture the microorganisms under the culturing temperature of 10 to 40° C., preferably 20 to 35° C., an air circulation rate of 0.1 to 2.0 VVM, preferably 0.1 to 1.5 VVM, a stirring rotation speed of 100 to 800 rpm, preferably 200 to 400 rpm, and a pH of 3.0 to 10.0, preferably 4.0 to 9.5.

The method of extracting the enzymes from the culture is not particularly limited in the present invention, though it is desirable to remove the bacterial cells by means of centrifugal separation, membrane filtration, etc. in the case of exoenzymes. It is desirable to carry out the centrifugal separation under a centrifugal force of 200 to 20,000×g. It is desirable to carry out the membrane filtration while controlling the pressure at 3.0 kg/m² or less by using an MF membrane or a filter press. In the case of endoenzymes, it is desirable to disintegrate the cells by using a homogenizer, a Waring blender, an ultrasonic disintegrator, a French press, a ball mill, etc. and to remove the cell residue by centrifugal separation, a membrane filtration, etc. The stirring rotating speed of the homogenizer should be 500 to 30,000 rpm, preferably 1,000 to 15,000 rpm. The Waring blender should be scanned at a rate of 500 to 5,000 rpm, preferably 1,000 to 10,000 rpm, and the stirring should be performed for 0.5 to 10 minutes, preferably 1 to 5 minutes. The ultrasonic disintegrator should be scanned at 1 to 50 KHz, preferably 10 to 20 KHz. Further, glass balls having a diameter of about 0.1 to 0.5 mm should desirably be used in the ball mill.

The phospholipid that is used as a component of the heat stabilizer of the invention is not particularly limited in the present invention, and includes, for example, a phospholipid derived from plant seeds, a phospholipid derived from animals, and a phospholipid prepared by an enzyme synthesis or a chemical synthesis. The plant seeds include, for example, rapeseeds, safflower seeds, soybean, corn, sesame seeds, and cotton seeds. The animal-derived phospholipid includes, for example, phospholipids derived from egg yolk and cattle brain. Further, the phospholipid prepared by enzyme synthesis or chemical synthesis, which is not particularly limited in the present invention, includes, for example, high purity products of PS (phosphatidyl serine), PI (phosphatidyl inositol), PA (phosphatidic acid), LPE (lysophosphatidyl ethanolamine), and LPC (lysophosphatidyl choline) that are produced by a base exchange reaction or hydrolytic reaction using phospholipase or a chemical synthesis. The kinds of the phospholipids, which are not particularly limited in the present invention, include, for example, PC (phosphatidyl choline), PE (phosphatidyl ethanol), PA, PI, and their lyso forms.

The oil-soluble vitamin that is used as another component of the heat stabilizer, which is not particularly limited in the present invention, should desirably be $\alpha$-, $\beta$-, $\gamma$-tocopherols, tocotrienol, retinol, calciferol, menaquinone, menadione, phylloquinone, ubiquinone and a mixture thereof.

For preparing a thermally stable enzyme composition of the present invention, an aqueous solution of an object enzyme is prepared, followed by adding a phospholipid and an oil-soluble vitamin to the aqueous solution for sufficiently mixing these components in the solution. Then, the enzyme aqueous solution having the heat stabilizer added thereto can be concentrated and converted into a powder.

An aqueous solution of the enzyme can be prepared by dissolving the dry enzyme powder in water. Alternatively, a supernatant of the enzyme culture solution or the extraction liquid itself can be used as the enzyme aqueous solution.

The enzyme concentration of the aqueous solution, which is not particularly limited in the present invention, should desirably be 0.01 to 90% by weight in the case of using a supernatant of the culture or the extraction liquid and 0.01 to 90% by weight in the case of using a dry enzyme powder.

To be more specific, in order to modify the surface of the enzyme with the heat stabilizer of the present invention, a phospholipid may be added in an amount of preferably 0.01 to 200% by weight, more preferably 1 to 8% by weight, of the enzyme weight to the aqueous solution of the object enzyme while maintaining the solution temperature at 0 to 25° C., preferably 0 to 5° C., and while stirring the solution with a homogenizer at 300 to 10,000 rpm for 1 to 30 minutes, preferably 1 to 5 minutes. Then, an oil-soluble vitamin may be added in an amount of preferably 0.01 to 100% by weight, more preferably 0.01 to 20% by weight, of the enzyme weight, to the solution while stirring the solution with a homogenizer at a rate of 100 to 8,000 rpm, preferably 1,000 to 6,000 rpm, for 1 to 20 minutes, preferably 1 to 5 minutes. The maximum yields of the concentrate and the powder depend on the concentration and kind of the enzyme, phospholipid and oil-soluble vitamin, making it possible to determine appropriately the concentrations of these components from within the ranges given above.

The enzyme composition of the present invention can be concentrated by a suitable concentrating method. For example, the concentration can be achieved by means of an evaporator, a flash evaporator, ultrafiltration (UF), membrane concentration, MF membrane concentration, salting-out with inorganic salts, precipitation using a solvent, adsorption using an ion-exchange cellulose or the like, and hygroscopic method using a hygroscopic gel. Particularly, a UF membrane concentration and concentration using an evaporator are preferably used. Concerning the module for the UF membrane concentration, it is desirable to use a plain membrane or a hollow fiber membrane having a fraction molecular weight of 3,000 to 100,000, preferably 6,000 to 50,000. It is also desirable to use a polyacrylonitrile material or a polysulfone material for forming the UF membrane. The concentration using an evaporator should desirably be performed under a heated temperature of 90° C. or less and a reduced pressure of 40 cmHg or less, more desirably under a heated temperature of 80° C. or less and a reduced pressure of 60 cmHg or less.

The enzyme composition of the present invention can be converted into a powder satisfactorily by any of drying under a reduced pressure, a freeze drying and a spray drying. It is desirable to employ a freeze drying or a spray drying in view of the activity recovery of the enzyme. The spray drying is particularly desirable if the production efficiency is also taken into account. The spray dryer includes, for example, a nozzle counter current type, a disc counter current type, a nozzle parallel flow type, and a disc parallel flow type. Preferably, it is desirable to use a disc parallel flow type spray dryer. For operating the spray dryer, it is desirable to control the rotating speed of the atomizer at 4,000 to 20,000 rpm, the inlet temperature at 100 to 200° C. and the outlet temperature at 40 to 100° C.

Examples and Comparative Examples will now be described to set forth more clearly the effect of the present invention. Of course, the present invention is not limited by the following Examples.

The heat stability and the remaining activity of each of the enzymes obtained in the Examples and Comparative Examples were evaluated by the methods given below:

[Heat Stability]

Where the enzyme was powdery, an aqueous solution containing 10% by weight of the enzyme was prepared. Where the enzyme was in the form of a liquid, the liquid enzyme was used as it was. Specifically, each of the aqueous solution and the liquid enzyme was put in a constant temperature bath maintained at 80° C. and sampled 10 minutes, 20 minutes and 30 minutes later to measure the remaining activity of the enzyme liquid, which was compared with a sample not subjected to the heat treatment.

[Remaining Activity]

75 milliliters (mL) of olive oil and 225 mL of 2% polyvinyl alcohol were put in a container of a homogenizer manufactured by Nippon Seiki K.K. and emulsified for 10 minutes under a rotating speed of 15,000 rpm while cooling the emulsion to 10° C. with ice. Then, 4 mL of a phosphoric acid buffer solution having a pH 7.0 was added to 5 mL of the resultant olive oil emulsion and the mixture was put in a test tube. Further, 1 mL of the enzyme liquid was put in the test tube to carry out reaction for 10 minutes at 37° C., followed by stopping the reaction with 2N HCl. Finally, the hydrolyzed free fatty acid was titrated with 2N NaOH using phenolphthalein as a color developing liquid. The remaining activity was calculated by comparison with the titration amount.

EXAMPLE 1

Strains of Alcaligenes species IFO 14130 were charged in an amount of 30 liters (L) in a fermenting vessel having an inner volume of 50 L and cultured for 36 hours under the conditions of 25° C. and 0.5 VVM using culture medium 1 given below to obtain 25 L of a fermented liquid. Then, 30% based on the enzyme weight of "BASIS LP-20" (trade name of a water-dispersible soybean phospholipid manufactured by Nisshin Oil Mils, containing 25–30 wt % of PC, 25–30 wt % of PE and 10–25 wt % of PI) and 10% of "MIXED TOCOPHEROL" (trade name of tocopherol manufactured by Nisshin Oil Mills) were added to a supernatant liquid prepared by centrifuging the culture solution for 15 minutes at 4,000×g. The mixture was stirred for 5 minutes by a homogenizer at 6,000 rpm while maintaining the mixture at 5° C. and, then, dried by a spray drying in which the inlet temperature and the outlet temperature were set at 190° C. and 95° C., respectively, to obtain 565 g of a lipase powder. The thermal stability was measured for each of the mixed liquid and the obtained powder, with the results as shown in Table 1. Incidentally, the supernatant liquid, to which the soybean phospholipid and the mixed tocopherols were not added, and 305 g of lipase powder obtained by spray-drying the supernatant liquid were used as references.

COMPARATIVE EXAMPLE 1

A mixed liquid was obtained as in Example 1 by adding 30% based on the enzyme weight of BASIS LP-20 to 25 L of a supernatant of the fermented liquid cultured as in Example 1. Also, 485 g of lipase powder was obtained by spray-drying the mixed liquid. The thermal stability was measured for each of the mixed liquid and the obtained powder, with the results as shown in Table 1.

COMPARATIVE EXAMPLE 2

A mixed liquid was obtained as in Example 1 by adding 10% of MIXED TOCOPHEROL to 25 L of a supernatant of the fermented liquid cultured as in Example 1. Also, 432 g of lipase powder was obtained by spray-drying the mixed liquid. The thermal stability was measured for each of the mixed liquid and the obtained powder, with the results as shown in Table 1.

EXAMPLE 2

Strains of *Penicillium cyclopium* ATCC-34613 were cultured in a triangular flask by using a culture medium 2 given below for 48 hours by a shaking culture under the conditions of 25° C. and 250 rpm. Then, bacteria were removed from the culture solution by compressive filtration, followed by adding 10% based on the enzyme weight of "BASIS LG-10" (trade name of a soybean phospholipid manufactured by Nisshin Oil Mills, containing 10–12 wt % of PC, 10–12 wt % of PE and 4–10 wt % of PI) and 5% by weight of DL-$\alpha$-tocopherol to the supernatant of the culture solution as in Example 1 to obtain a mixed liquid. The thermal stability of the mixed liquid was measured, with the result as shown in Table 2.

COMPARATIVE EXAMPLE 3

10% by weight of TWEEN 80 and 5% by weight of DL-$\alpha$-tocopherol were mixed as in Example 1 with a supernatant of a fermented liquid cultured as in Example 2 to obtain a mixed liquid. The thermal stability of the mixed liquid was measured, with the result as shown in Table 2.

COMPARATIVE EXAMPLE 4

5% by weight of DL-$\alpha$-tocopherol and 40% by weight of "SY GLYSTER MSW-750" (trade name of monoglyceride manufactured by Sakamoto Yakuhin Kogyo K.K.) were mixed as in Example 1 with a supernatant of a fermented liquid cultured as in Example 2 to obtain a mixed liquid. The thermal stability of the mixed liquid was measured, with the result as shown in Table 2.

COMPARATIVE EXAMPLE 5

5% by weight of DL-$\alpha$-tocopherol and 2% by weight of "DK ESTER FOR" (trade name of a sugar ester manufactured by Dai-ichi Kogyo Seiyaku K.K.) were mixed as in Example 1 with a supernatant of a fermented liquid cultured as in Example 2 to obtain a mixed liquid. The thermal stability of the mixed liquid was measured, with the result as shown in Table 2.

EXAMPLE 3

Strains of *Geotrichum candidum* ATCC-3461 were charged in an amount of 30 L in a fermenting vessel having an inner volume of 50 L and cultured for 24 hours by using culture medium 4 given below under the conditions of 25° C., 1 VVM and a stirring rotation speed of 300 rpm. The culture solution was centrifuged for 15 minutes at 3500×g, and the resultant supernatant was used as an enzyme liquid. Then, 30% by weight based on the enzyme weight of "SLP-WATER SOLUBLE LECITHIN" manufactured by True Lecithin Kogyo K.K. (having a composition similar to BASIS LP-20) and 10% by weight of α-tocopherol were mixed as in Example 1 with the enzyme liquid to obtain a mixed enzyme liquid. A thermal stability test was applied to the mixed enzyme liquid, with the result as shown in Table 3.

EXAMPLE 4

A mixed enzyme liquid was prepared by mixing egg yolk phospholipid and γ-tocopherol as in Example 1 with an enzyme liquid prepared as in Example 3. A thermal stability test was applied to the mixed enzyme liquid, with the result as shown in Table 3.

EXAMPLE 5

A mixed enzyme liquid was prepared by mixing cow brain phospholipid (50% PS) and mixed tocopherols as in Example 1 with an enzyme liquid prepared as in Example 3. A thermal stability test was applied to the mixed enzyme liquid, with the result as shown in Table 3.

EXAMPLE 6

A mixed enzyme liquid was prepared by mixing rapeseed phospholipid and "LECHINOL" (trade name of vitamin A oil manufactured by Kanematsu Shokuhin K.K.) as in Example 1 with an enzyme liquid prepared as in Example 3. A thermal stability test was applied to the mixed enzyme liquid, with the result as shown in Table 3.

EXAMPLE 7

A mixed enzyme liquid was prepared by mixing a soybean-derived "SUN-LECITHIN A-1" (trade name of an enzyme-decomposed lecithin manufactured by Taiyo Kagaku K.K., having a composition similar to Basis LP-20) and "DRY VITAMIN D" (trade name of Calciferol manufactured by Sankyo K.K.) as in Example 1 with an enzyme liquid prepared as in Example 3. A thermal stability test was applied to the mixed enzyme liquid, with the result as shown in Table 3.

EXAMPLE 8

Strains of *Aspergillus niger* NRRL-337 were charged in an amount of 300 L in a fermenting vessel having an inner volume of 500 L and cultured for 48 hours by using culture medium 3 given below under the conditions of 25° C., 1 VVM and a stirring rotation speed of 300 rpm. The culture solution was filtered by a compressive filtration to recover 260 L of a supernatant having bacteria removed therefrom. The supernatant was concentrated to 30 L by a UF membrane module having a fraction molecular weight of 3000 and made of a hollow string membrane of polyacrylonitrile series. The concentrated supernatant was diluted with 230 L of city water, followed by similarly concentrating the dilute supernatant to 35 L. Then, 40% by weight based on the enzyme weight of "LECITHIN DELUXE" (trade name of lecithin manufactured by Nisshin Oil Mills) and 10% by weight based on the enzyme weight of "TOCOPHEROL 85" manufactured by Nisshin Oil Mills were mixed as in Example 1 with the desalted concentrated solution. The mixed concentrated solution was subjected to a spray drying under the inlet temperature of 195° C., the outlet temperature of 95° C., and an evaporation rate of 10 L/hr to obtain 4.5 kg of a lipase powder. The activity recovery rate of the powder was 75.8%. A thermal stability test was applied to the lipase powder, with the result as shown in Table 4.

COMPARATIVE EXAMPLE 6

A mixed concentrated solution was obtained as in Example 8 and, then, subjected to a freeze-drying for 48 hours by using a freeze-dryer under a reduced pressure of 70 cmHg, and heating of the stacked shelving to 40° C. to obtain 4.8 kg of a lipase powder. The activity recovery rate of the powder was 72.9%. A thermal stability test was applied to the lipase powder, with the result as shown in Table 4.

COMPARATIVE EXAMPLE 7

A mixed concentrated solution was obtained as in Example 8. Then, acetone cooled to −20° C. was added to the mixed concentrated solution in an amount equal to that of the mixed concentrated solution (1:1). The mixture was kept stirred for 3 hours with a stirrer, followed by subjecting the precipitate to a suction filtration by using a filtering paper (type A). The precipitate was recovered and, then, subjected to a vacuum drying under a pressure of 70 cmHg or more to obtain 2.4 kg of a lipase powder. The activity recovery rate of the powder was 33.9%. A thermal stability test was applied to the lipase powder, with the result as shown in Table 4.

EXAMPLE 9

Strains of *Candida cylindracea* NRRL Y-1469 were charged in an amount of 30 L in a fermenting vessel having an inner volume of 50 L and cultured for 24 hours by using culture medium 4 given below under the conditions of 25° C., 1 VVM and a stirring rotation speed of 400 rpm. The culture solution was centrifuged for 15 minutes at 3,000×g to obtain 25 L of a supernatant. The supernatant was concentrated by an evaporator heated to 80° C. under a reduced pressure of 60 cmHg to obtain 3 L of a concentrated solution. 40% by weight based on the enzyme amount and 20% by weight of a powdery vitamin D manufactured by Kanematsu Shokuhin K.K. were mixed as in Example 1 with the concentrated solution. The mixture was subjected to a spray drying under the inlet temperature of 195° C., the outlet temperature of 95° C. and an evaporation rate of 10 L/hr to obtain 450 g of a lipase powder. A thermal stability test was applied to each of the mixed concentrated solution and the lipase powder, with the results as shown in Table 5.

EXAMPLE 10

Strains of Streptomyces species IFO 3110 were charged in an amount of 30 L in a fermenting vessel having an inner volume of 50 L and cultured for 48 hours by using culture medium 5 given below under the conditions of 25° C., 1 VVM and a stirring rotation speed of 300 rpm. The culture solution was centrifuged for 10 minutes at 6,000×g to obtain 24 L of a supernatant. The supernatant was concentrated by an evaporator under heating at 80° C. and a reduced pressure of 60 cmHg to obtain 3 L of a concentrated solution. Then, 10% by weight based on the enzyme weight of Basis LP-20 manufactured by Nisshin Oil Mills and 10% by weight of MIXED TOCOPHEROL were mixed as in Example 1 with the concentrated solution. The mixed concentrated solution was subjected to a spray drying under the inlet temperature of 195° C., the outlet temperature of 95° C. and an evaporation rate of 10 L/hr to obtain 480 g of phospholipase powder. A thermal stability test was applied to the mixed concentrated solution and to the phospholipase powder, with the results as shown in Table 5.

EXAMPLE 11

Strains of *Xanthomonas campestris* NRRL-B1459 were charged in 10 triangular flasks each having an inner volume of 3 L, the charging amount being 1 L for each flask, and cultured for 48 hours at 30° C. by using the culture medium 1 under a stirring rotation speed of 250 rpm. The culture solution was centrifuged for 15 minutes at 6000 rpm to obtain a supernatant, which was cooled to 4° C. with ice. Then, 40% by weight based on the enzyme amount of "SLP-PC35" (trade name of soybean phospholipid manufactured by True Lecithin K.K.) and 50% by weight of vitamin AD oil manufactured by Takeda Yakuhin Kogyo K.K. were mixed with the cooled supernatant. The mixture was kept stirred with a stirrer for 24 hours while cooling the mixture to 4° C. with ice, followed by subjecting the mixture to a spray drying under the inlet temperature of 191° C., the outlet temperature of 95° C. and a water evaporation rate of 5 L/hr to obtain 880 g of an esterase powder enzyme. A thermal stability test was applied to each of the mixed concentrated solution and the esterase powder enzyme, with the results as shown in Table 5.

EXAMPLE 12

Each of lipases available on the market, i.e., LIPASE OF (trade name of lipase manufactured by Meito Sangyo K.K.), LIPASE PL (trade name of lipase manufactured by Meito Sangyo K.K.), PARATASE (trade name of lipase manufactured by Novo Nordisk Ltd.) and LIPASE D (trade name of lipase manufactured by Amano Seiyaku K.K.), was dissolved in city water to prepare an enzyme solution containing 10% by weight of the enzyme. Then, 30% by weight of β-tocopherol and 10% by weight of LECITHIN DELUXE were mixed with the enzyme solution, and the mixed solution was kept stirred with a stirrer for 24 hours while maintaining the solution temperature at 4° C. A thermal stability test was applied to the mixed solution and to a control case where an oil-soluble vitamin was not added to the enzyme solution. Table 6 shows the results.

EXAMPLE 13

Strains of *Bacillus subtilis* ATCC-4529 were cultured for 36 hours at 30° C. in a fermenting vessel having an inner volume of 50 L by using culture medium 6 given below under a stirring rotation speed of 300 rpm and 1 VVM. The culture solution was centrifuged at 4,000 rpm for 10 minutes to obtain 23 L of a supernatant. Then, 40% by weight based on the enzyme amount of BASIS LP-20 and 30% by weight of ubiquinone were mixed with the supernatant, and the mixture was kept stirred with a stirrer for 24 hours while cooling the mixture at 4° C. with ice. The mixed solution was subjected to a spray drying under the inlet temperature of 185° C. and the outlet temperature of 95° C. to obtain 1350 g of subtilisin (serine protease) powder. For measuring the enzyme activity, 1 mL of the enzyme was added to 3 mL of 3/4% milk casein dissolved in 0.05M buffer solution having a pH 11.0 for carrying out the reaction for 10 minutes at 37° C. Then, the reaction was stopped by using trichloroacetic acid. The enzyme activity was calculated by measuring the absorbance of 660 nm. Incidentally, the enzyme 1U represents the enzyme amount required for forming 1 μmol of tyrosine in a minute. Table 7 shows the results.

EXAMPLE 14

Strains of *Lactobacillus acidophilus* IFO-1395 were cultured at 37° C. for 48 hours in a fermenting vessel having an inner volume of 50 L under a stirring rotation speed of 300 rpm and 1 VVM. The culture solution was centrifuged at 4,000 rpm for one minute to obtain 22 L of a supernatant. Then, 30% by weight based on the enzyme weight of BASIS LG-20P (trade name of lecithin manufactured by Nisshin Oil Mills) and 40% by weight of phylloquinone were mixed with the supernatant, and the mixture was kept stirred for 12 hours while cooling the mixture to 4° C. with ice. The mixed solution was subjected to a spray drying at the inlet temperature of 195° C. and the outlet temperature of 98° C. to obtain 1.85 kg of β-galactosidase powder. For measuring the enzyme activity, a substrate solution was prepared by dissolving 0.0025 M of o-nitrophenyl-1-galactoside in 1/10 M phosphoric acid buffer solution having a pH 7.0. Then, 1 mL of the enzyme solution was added to 4 mL of the substrate solution for carrying out the reaction at 40° C. for 10 minutes, followed by stopping the reaction using sodium carbonate. The enzyme activity was calculated by measuring the absorbance of 420 nm. The enzyme 1U represents an enzyme amount that permits liberating 1 μmol of o-nitrophenol in a minute. Table 8 shows the results.

| Raw materials | (%) |
|---|---|
| [culture medium 1] | |
| Soybean powder | 2.0 |
| $K_2HPO_4$ | 0.2 |
| $(NH_4)_2SO_4$ | 1.0 |
| Peptone | 1.0 |
| [culture medium 2] | |
| Corn steep liquor | 2.0 |
| Soybean powder | 1.0 |
| $K_2HPO_4$ | 0.5 |
| $(NH_4)_2SO_4$ | 0.1 |
| $MgSO_4 \cdot 7H_2O$ | 0.1 |
| [culture medium 3] | |
| Soybean powder | 3.0 |
| Peptone | 1.0 |
| $K_2HPO_4$ | 0.2 |
| $(NH_4)_2SO_4$ | 0.1 |
| [culture medium 4] | |
| Soybean powder | 2.0 |
| Corn steep liquor | 3.0 |
| $K_2HPO_4$ | 0.5 |
| $(NH_4)_2SO_4$ | 0.2 |
| Tween80 | 0.3 |

-continued

| Raw materials | (%) |
|---|---|
| [culture medium 5] | |
| Soybean powder | 3.0 |
| Peptone | 1.5 |
| $K_2HPO_4$ | 0.5 |
| $(NH_4)_2SO_4$ | 0.2 |
| Lecithin Deluxe | 0.3 |
| [culture medium 6] | |
| Glucose | 5.0 |
| Soybean powder | 2.0 |
| Milk casein | 2.0 |
| $K_2HPO_4$ | 0.25 |
| $MgSO_4 \cdot 7H_2O$ | 0.25 |
| Soyaflower A | 2.0 |
| (de-fatted soybean) | adjusted to pH 7.0 |
| [culture medium 7] | |
| Polypeptone | 10.0 |
| Yeast extract | 5.0 |
| $K_2HPO_4$ | 2.5 |
| Anhydrous sodium acetate | 10.0 |
| Lactose | 10.0 |
| | adjusted to pH6.8 |

TABLE 1

Thermal stability of lipase

| | | Enzyme activity remaining rate | | | |
|---|---|---|---|---|---|
| | | 0 minute | 10 minutes | 20 minutes | 30 minutes |
| Example 1 | Mixed solution | 100 | 100 | 95 | 85 |
| | Powder | 100 | 100 | 90 | 83 |
| Comparative Example 1 | Mixed solution | 100 | 35 | 21 | 20 |
| | Powder | 100 | 30 | 21 | 21 |
| Comparative Example 2 | Mixed solution | 100 | 30 | 20 | 20 |
| | Powder | 100 | 38 | 23 | 21 |
| Control | Mixed solution | 100 | 21 | 15 | 9 |
| | Powder | 100 | 10 | 5 | 5 |

TABLE 2

Thermal stability dependent on difference in emulsifier

| | Enzyme activity remaining rate | | | |
|---|---|---|---|---|
| | 0 minute | 10 minutes | 20 minutes | 30 minutes |
| Example 2 | 100 | 100 | 88 | 81 |
| Comparative Example 3 | 100 | 32 | 31 | 31 |
| Comparative Example 4 | 100 | 23 | 21 | 18 |
| Comparative Example 5 | 100 | 25 | 20 | 15 |

TABLE 3

Comparison of thermal stability dependent on difference in phospholipid and oil-soluble vitamin

| | Enzyme activity remaining rate | | | |
|---|---|---|---|---|
| | 0 minute | 10 minutes | 20 minutes | 30 minutes |
| Example 3 | 100 | 100 | 93 | 83 |
| Example 4 | 100 | 100 | 91 | 85 |
| Example 5 | 100 | 100 | 88 | 81 |
| Example 6 | 100 | 100 | 95 | 82 |
| Example 7 | 100 | 100 | 91 | 83 |

TABLE 4

Comparison in thermal stability and activity yield under each drying method

| | Enzyme activity remaining rate | | | | |
|---|---|---|---|---|---|
| | 0 minute | 10 minutes | 20 minutes | 30 minutes | Heat recovery Rate (%) |
| Example 8 | 100 | 95 | 88 | 76 | 75.8 |
| Comparative Example 6 | 100 | 98 | 92 | 83 | 72.9 |
| Comparative Example 7 | 100 | 99 | 88 | 74 | 33.9 |

TABLE 5

Thermal stability for each manufacturing method

| | | Enzyme activity remaining rate | | | |
|---|---|---|---|---|---|
| | | 0 minute | 10 minutes | 20 minutes | 30 minutes |
| Example 9 | Mixed concentrated solution | 100 | 100 | 91 | 88 |
| | Enzyme powder | 100 | 98 | 92 | 83 |
| Comparative Example 10 | Mixed concentrated solution | 100 | 100 | 93 | 81 |
| | Enzyme powder | 100 | 99 | 88 | 74 |

TABLE 5-continued

Thermal stability for each manufacturing method

| | | Enzyme activity remaining rate | | | |
|---|---|---|---|---|---|
| | | 0 minute | 10 minutes | 20 minutes | 30 minutes |
| Comparative | Mixed concentrated solution | 100 | 100 | 90 | 71 |
| Example 11 | Enzyme powder | 100 | 88 | 75 | 70 |

TABLE 6

Thermal stability test for enzymes available on the market

| | Enzyme activity remaining rate | | | |
|---|---|---|---|---|
| | 0 minute | 10 minutes | 20 minutes | 30 minutes |
| Lipase PL mixed solution | 100 | 100 | 90 | 85 |
| (no addition, control) | 100 | 15 | 11 | 11 |
| Lipase OF mixed solution | 100 | 88 | 80 | 75 |
| (no addition, control) | 100 | 23 | 21 | 8 |
| Paratase mixed solution | 100 | 90 | 85 | 80 |
| (no addition, control) | 100 | 21 | 20 | 12 |
| Lipase D mixed solution | 100 | 100 | 88 | 79 |
| (no addition, control) | 100 | 11 | 7 | 5 |

TABLE 7

Stability of protease

| | | Enzyme activity remaining rate | | | |
|---|---|---|---|---|---|
| | | 0 minute | 10 minutes | 20 minutes | 30 minutes |
| Example 13 | concentrated enzyme solution | 100 | 100 | 100 | 93 |
| | Enzyme powder | 100 | 100 | 99 | 95 |
| | control (no addition) | 100 | 82 | 72 | 55 |

TABLE 8

Thermal stability of sugar-decomposing enzyme

| | | Enzyme activity remaining rate | | | |
|---|---|---|---|---|---|
| | | 0 minute | 10 minutes | 20 minutes | 30 minutes |
| Example 14 | concentrated enzyme solution | 100 | 100 | 95 | 83 |
| | enzyme powder | 101 | 100 | 100 | 89 |
| | control (no addition) | 100 | 81 | 75 | 51 |

As described above, a phospholipid and an oil-soluble vitamin are added to an enzyme in the present invention. As a result, the thermal stability of the enzyme in an aqueous system is markedly improved. Also, since a sufficient enzyme activity at high temperatures can be obtained in the enzyme reaction and the activity is stable, the enzyme synthesis can be performed by using a substrate having a high melting point. Further, since the enzyme solution can be concentrated and converted into an enzyme powder under heat, the enzyme powder can be prepared efficiently.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A thermally stable enzyme composition, comprising an enzyme and a heat stabilizer comprising a phospholipid and an oil-soluble vitamin, said enzyme is selected from the group consisting of lipoprotein lipase, monoacyl, glycerol lipase, diacyl glycerol lipase, triacyl glycerol lipase, and galactolipase.

2. The composition according to claim 1, wherein said phospholipid is contained in an amount of from 0.01 to 200% by weight and said oil-soluble vitamin is continued in an amount of from 0.01 to 100% by weight, based on the enzyme weight.

3. The composition according to claim 1, wherein said oil-soluble vitamin is at least one compound selected from the group consisting of tocopherol, tocotrienol, retinal, calciferol, phylloquinone, and ubiquinone.

4. The composition according to claim 1 wherein said phospholipid is at least one compound selected from the group consisting of phosphatidyl choline, phosphatidyl ethanol, phosphatidic acid, phosphatidyl inositol, phosphatidyl serine and lyso forms thereof.

5. The composition according to claim 1, which is in the form of a powder.

6. A thermally stable enzyme composition, comprising an enzyme and a heat stabilizer comprising a phospholipid and an oil-soluble vitamin, said enzyme is a glycosylase selected from the group consisting of amylase, glucosidase, cellulase, xylanase, dexdtranase, chitinase, lysozyme, galactosidase, mannosidase, glucuronidase, hyaluronidase, and pectin lyase.

7. The composition according to claim 6, wherein said phospholipid is contained in an amount of from 0.01 to 200% by weight and said oil-soluble vitamin is continued in an amount of from 0.01 to 100% by weight, based on the enzyme weight.

8. The composition according to claim 6, wherein said oil-soluble vitamin is at least one compound selected from the group consisting of tocopherol, tocotrienol, retinal, calciferol, phylloquinone, and ubiquinone.

9. The composition according to claim 6, wherein said phospholipid is at least one compound selected from the group consisting of phosphatidyl choline, phosphatidyl ethanol, phosphatidic acid, phosphatidyl inositol, phosphatidyl serine and lyso forms thereof.

10. The composition according to claim 6, which is in the form of a powder.

11. A thermally stable enzyme composition, comprising an enzyme and a heat stabilizer comprising a phospholipid and an oil-soluble vitamin, said enzyme is a protease selected from the group consisting of acid proteinase, serine protease, cysteine protease, dipeptidylamino peptidase, and dipeptidylcarboxy peptidase.

12. The composition according to claim 11, wherein said phospholipid is contained in an amount of from 0.01 to 200% by weight and said oil-soluble vitamin is continued in an amount of from 0.01 to 100% by weight, based on the enzyme weight.

13. The composition according to claim 11, wherein said oil-soluble vitamin is at least one compound selected from the group consisting of tocopherol, tocotrienol, retinal, calciferol, phylloquinone, and ubiquinone.

14. The composition according to claim 11 wherein said phospholipid is at least one compound selected from the group consisting of phosphatidyl choline, phosphatidyl ethanol, phosphatidic acid, phosphatidyl inositol, phosphatidyl serine and lyso forms thereof.

15. The composition according to claim 11, which is in the form of a powder.

16. A thermally stable enzyme composition, comprising an enzyme and a heat stabilizer comprising a phospholipid and an oil-soluble vitamin, said phospholipid being present in an amount of from 1 to 8% by weight based on the weight of the enzyme, said oil-soluble vitamin being present in an amount of from 0.01 to 20% by weight based on the weight of the enzyme and wherein said enzyme is a lipase selected from the group consisting of lipoprotein lipase, monoacyl glycerol lipase, diacyl glycerol lipase, triacyl, glycerol lipase, and galactolipase.

17. The composition according to claim 16, wherein said oil-soluble vitamin is at least one compound selected from the group consisting of tocopherol, tocotrienol, retinol, calciferol, phylloquinone, and ubiquinone.

18. The composition according to claim 16, wherein said phospholipid is at least one selected from the group consisting of phosphatidyl choline, phosphatidyl ethanol, phosphatidic acid, phosphatidyl inositol, phosphatidyl serine and lyso forms thereof.

19. The composition according to claim 16, which is in powder form.

20. A thermally stable enzyme composition, comprising an enzyme and a heat stabilizer comprising a phospholipid and an oil-soluble vitamin, said phospholipid being present in an amount of from 1 to 8% by weight based on the weight of the enzyme, said oil-soluble vitamin being present in an amount of from 0.01 to 20% by weight based on the weight of the enzyme and wherein said enzyme is a glycosylase selected from the group consisting of amylase, glucosidase, cellulase, xylanase, dextranase, chitinase, lysozyme, galactosidase, mannosidase, glucuronidase, hyaluronidase, and pectin lyase.

21. The composition according to claim 20, wherein said oil-soluble vitamin is at least one compound selected from the group consisting of tocopherol, tocotrienol, retinol, calciferol, phylloquinone, and ubiquinone.

22. The composition according to claim 20, wherein said phospholipid is a at least one selected from the group consisting of phosphatidyl choline, phosphatidyl ethanol, phosphatidic acid, phosphatidyl inositol, phosphatidyl serine and lyso forms thereof.

23. The composition according to claim 20, which is in powder form.

24. A thermally stable enzyme composition, comprising an enzyme and a heat stabilizer comprising a phospholipid and an oil-soluble vitamin, said phospholipid being present in an amount of from 1 to 8% by weight based on the weight of the enzyme, said oil-soluble vitamin being present in an amount of from 0.01 to 20% by weight based on the weight of the enzyme and wherein said enzyme, is a protease selected from the group of acid proteinase, serine protease, cysteine protease, and dipeptidylcarboxy peptidase.

25. The composition according to claim 24, wherein said oil-soluble vitamin is at least one compound selected from the group consisting of tocopherol, tocotrienol, retinol, calciferol, phylloquinone, and ubiquinone.

26. The composition according to claim 24, wherein said phospholipid is at least one selected from the group consisting of phosphatidyl choline, phosphatidyl ethanol, phosphatidic acid, phosphatidyl inositol, phosphatidyl serine and lyso forms thereof.

27. The composition according to claim 24, which is in powder form.

* * * * *